(12) United States Patent
Casstevens et al.

(10) Patent No.: US 7,709,821 B2
(45) Date of Patent: May 4, 2010

(54) FLOW CYTOMETER ACQUISITION AND DETECTION SYSTEM

(75) Inventors: Martin K. Casstevens, Amherst, NY (US); Ryszard Burzynski, Kenmore, NY (US); John Weibel, Tonawanda, NY (US); Alexander Kachynski, Amherst, NY (US)

(73) Assignee: Advanced Cytometry Instrumentation Systems, Inc., Amherst, NY (US)

( * ) Notice: Subject to any disclaimer, the term of this patent is extended or adjusted under 35 U.S.C. 154(b) by 186 days.

(21) Appl. No.: 11/380,434

(22) Filed: Apr. 27, 2006

(65) Prior Publication Data

US 2006/0273260 A1 Dec. 7, 2006

Related U.S. Application Data

(60) Provisional application No. 60/675,255, filed on Apr. 27, 2005.

(51) Int. Cl.
*G01N 21/49* (2006.01)
*G01J 1/58* (2006.01)

(52) U.S. Cl. .................................. 250/573; 250/458.1

(58) Field of Classification Search ............ 250/227.14, 250/458.1, 574, 573, 575, 222.2; 385/12, 385/115, 13; 356/328, 326, 14, 73.1, 337–343; 600/477, 476
See application file for complete search history.

(56) References Cited

U.S. PATENT DOCUMENTS

| 3,864,044 | A | * | 2/1975 | Lyshkow | 356/436 |
|---|---|---|---|---|---|
| 4,173,415 | A | * | 11/1979 | Wyatt | 356/336 |
| 5,491,344 | A | * | 2/1996 | Kenny et al. | 250/461.1 |
| 5,828,452 | A | * | 10/1998 | Gillispie et al. | 356/328 |
| 5,856,870 | A | * | 1/1999 | Curtiss | 356/328 |
| 6,204,919 | B1 | * | 3/2001 | Barshad et al. | 356/326 |
| 6,381,018 | B1 | * | 4/2002 | Bigio et al. | 356/432 |
| 7,245,379 | B2 | * | 7/2007 | Schwabe | 356/436 |
| 7,420,674 | B2 | * | 9/2008 | Gerstner et al. | 356/318 |
| 2002/0103439 | A1 | * | 8/2002 | Zeng et al. | 600/476 |
| 2004/0071332 | A1 | * | 4/2004 | Bruce et al. | 382/133 |
| 2004/0240063 | A1 | * | 12/2004 | Delage et al. | 359/571 |
| 2005/0151966 | A1 | * | 7/2005 | Packirisamy et al. | 356/328 |
| 2005/0175273 | A1 | * | 8/2005 | Iida et al. | 385/15 |
| 2005/0275839 | A1 | * | 12/2005 | Robinson et al. | 356/318 |

* cited by examiner

*Primary Examiner*—Que T Le
*Assistant Examiner*—Jennifer Bennett
(74) *Attorney, Agent, or Firm*—Hodgson Russ LLP

(57) ABSTRACT

A flow cytometer has a flow cell through which a sample flows and at least one laser emitting an excitation beam for illuminating a corresponding interrogation region in the flow cell. Scattered and fluorescence light from each interrogation region is collected by one or more input fibers for that region, and the input fiber(s) are fed to a dispersion module for that interrogation region that disperses the incoming light into different spectral regions. The dispersed light is conveyed, such as by a plurality of output fibers, to one or more photosensitive detectors. Thus, time multiplexed light signals may be delivered to a detector whereby several unique light signals can be measured by a single detector.

18 Claims, 11 Drawing Sheets

FLOW CYTOMETER ACQUISITION AND DETECTION SYSTEM

CROSS REFERENCE TO RELATED APPLICATIONS

This application claims benefit of U.S. Provisional Application Ser. No. 60/675,255 filed Apr. 27, 2005, which is hereby incorporated by reference herein.

STATEMENT REGARDING FEDERALLY SPONSORED RESEARCH

This work was supported by Grant No. DE-FG02-01ER83134 from the Department of Energy. The United States Government has certain rights in the invention.

FIELD OF THE INVENTION

The invention relates to the field of flow cytometry.

BACKGROUND OF THE INVENTION

Flow cytometry is a technique wherein light (usually focused laser beams) of specific wavelengths is used to illuminate cells, beads, macromolecules, etc. as they flow in a narrow stream. Scattered light is collected in the forward and side directions to provide information relating to the size, structure, etc. of the particles.

A common practice in flow cytometry is to employ highly fluorescent dyes to label cells in specific ways. One common method is to attach these dyes to biologically active molecules such as antibodies which selectively attach themselves to specific sites on or inside of cells. In this way, cells having these binding sites will be labeled and demonstrate fluorescence of a particular emission color when illuminated by light of the appropriate wavelength.

Regardless of how these dyes find themselves associated with cells, the strength of the measured signal is to a first approximation proportional to the amount of dye present with the cell. This method of labeling cells is now widespread in the study of biological specimens and is routinely done in samples prepared for fluorescent microscopes, flow cytometers, or other applications.

Flow cytometers are unique among many of these instruments because they do not make aggregate measurements (signals coming from a number of cells). While fluorescent microscopy can also examine single cells, the process is usually characterized by small sample sizes, and poor quantitation.

It is common to use more than one fluorescent dye in an effort to gain additional information about the cells as they pass through the illuminating light beam. To distinguish the signals from each other, the fluorescent labels are typically chosen so that they can be excited by the same light source, but fluoresce at different colors which can be separated using one or more techniques. Most dyes have a range of wavelengths at which they can be excited from their ground state to excited states. These molecules emit light over a range of wavelengths which is red shifted with respect to the illumination source when they return to their ground state.

To more efficiently distinguish between different fluorescent light signals, the emission spectra of different dyes are chosen so there is little or no spectral overlap. A technique known as FRET (fluorescence resonance energy transfer) uses dye combinations to tune the emission spectra further away from the excitation light and thereby increase the range over which fluorescent signals can be distributed in the electromagnetic spectrum. Dyes that have narrower emissions are preferred to those with broad emissions since their use permits more dyes to be used at the same time. Armed with knowledge of the dyes' emission spectra, it is possible and practical to account or compensate for the influence of a spectrally adjacent dye on another dye's signal provided the emission overlap is not too great.

It is a common desire for flow cytometer practitioners to use several fluorescent labels at the same time. Rather than attempting to fit all these dyes along the electromagnetic spectrum without excessive emission overlap, a common technique is to use multiple light sources spatially separated along the stream of flowing cells. In this manner dyes that have the same emission spectra, but different excitation spectra can be used to label the cells and the signals can be more easily distinguished.

A common flow cytometer design is to collect the signal light from all spatially separated interrogation regions and use wavelength dependent mirrors to separate the differently colored light signals. Apertures can be used to pass the light coming from a single interrogation region. In this manner, each detector would be used to detect a specific wavelength range coming from a single interrogation region. Using this type of arrangement common in flow cytometry, it takes n detectors to measure n different wavelength signals.

The systems described above typically employ free space optics. Recently, some commercial flow cytometers have employed a linear array of optical fibers to separate light from different interrogation regions. The image of the flow cell is focused onto the input plane of a linear array of optical fibers. In this manner, light from each interrogation region enters a unique fiber.

Each of these fibers then delivers the light from a single interrogation region to an arrangement of wavelength dependent mirrors to direct light of different wavelength ranges each to a different detector. These arrangements of wavelength dependent mirrors are larger than desired (owing to the size of beam diameters, mirrors, and detector housings). Each of these arrangements require n detectors to measure n signals.

The wavelength dependent mirrors are arranged such that incident light is not normal to them, but rather at some other angle. To the extent that incident light is not normal, the spectral properties of the mirror change and more importantly, the s and p polarizations tend to have different reflection/transmission properties. Since the signal light in a flow cytometer is unpolarized, the transitions between reflected wavelengths and transmitted wavelengths become less sharp at off-normal incidence. To address this fact, manufacturers have tended to increase the path length between wavelength selective mirrors to approach a closer-to-normal angle of incidence. While effective, the system becomes larger in size and more sensitive to misalignments and airborne dust.

SUMMARY OF THE INVENTION

This application describes innovations to a flow cytometer's signal light collection/distribution and detection system which fundamentally change the way signals are detected. There are important new applications stemming from this technology and serious reductions in required space and component costs. The system is flexible in operation, modular and expandable.

This patent application describes how the image of a flow cell can be focused onto a linear fiber array where each interrogation region is optically coupled with a different input fiber of the linear fiber array. The input fibers are multimode fibers (larger core diameter) and have numerical apertures which are compatible with the light collection and focusing lenses to facilitate greater coupling efficiencies. The individual input fibers are separated and fed into a dispersion module which disperses multiwavelength light signals. These signals are coupled into an array of output fibers, each containing a specific wavelength range, which are then directed to a set of detectors. The proposed arrangement involves fewer optical interfaces, which reduces optical losses, is more compact, more easily reconfigured, more robust, less prone to airborne dust, and can be made less expensively. This method permits time multiplexed signals to be delivered to detectors permitting several unique signals to be measured by a single detector.

BRIEF DESCRIPTION OF THE DRAWINGS

The invention will be explained in more detail, by way of example, with reference to the figures in which.

DETAILED DESCRIPTION OF THE INVENTION

Figure 1:
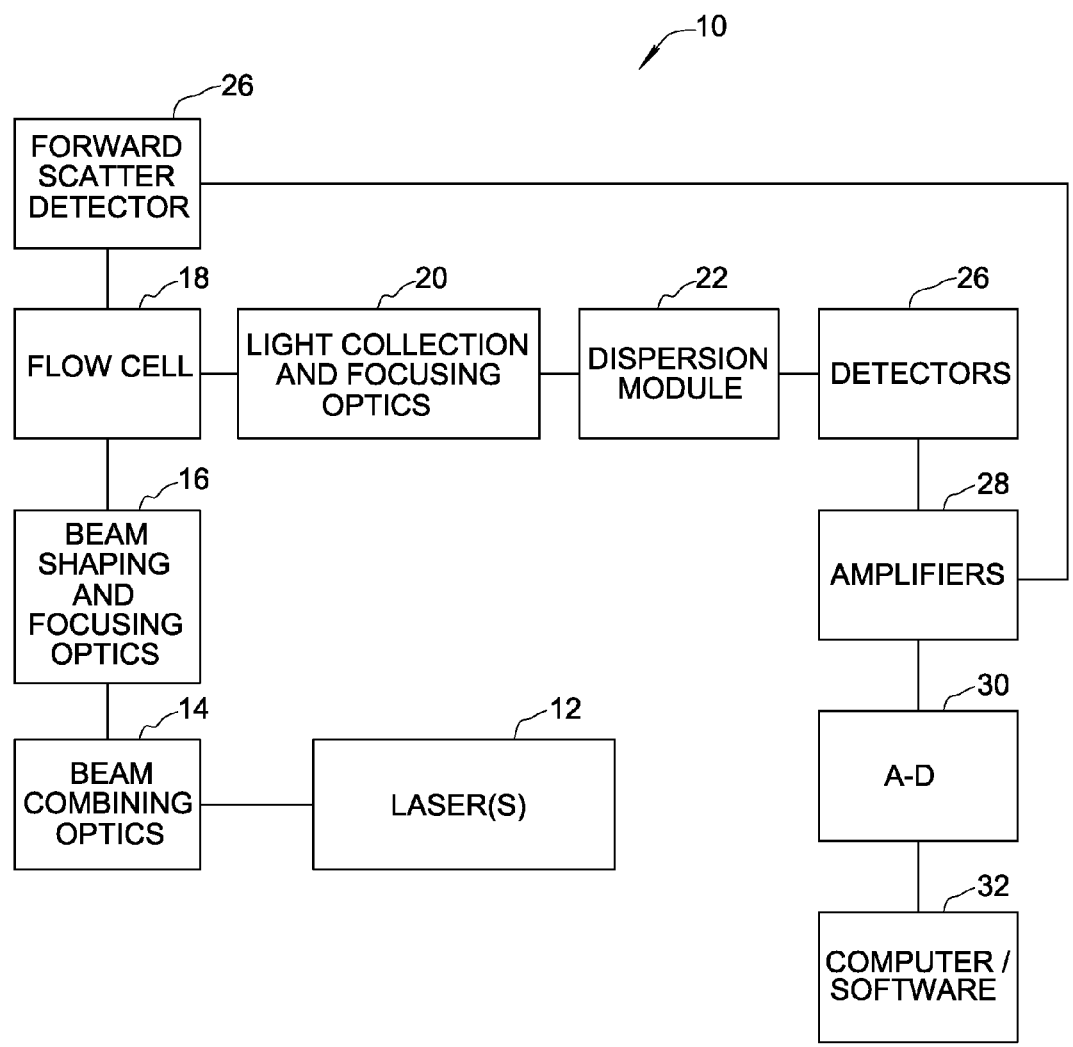
FIG. 1 is a block diagram illustrating an embodiment of the present invention.
Figure 2:
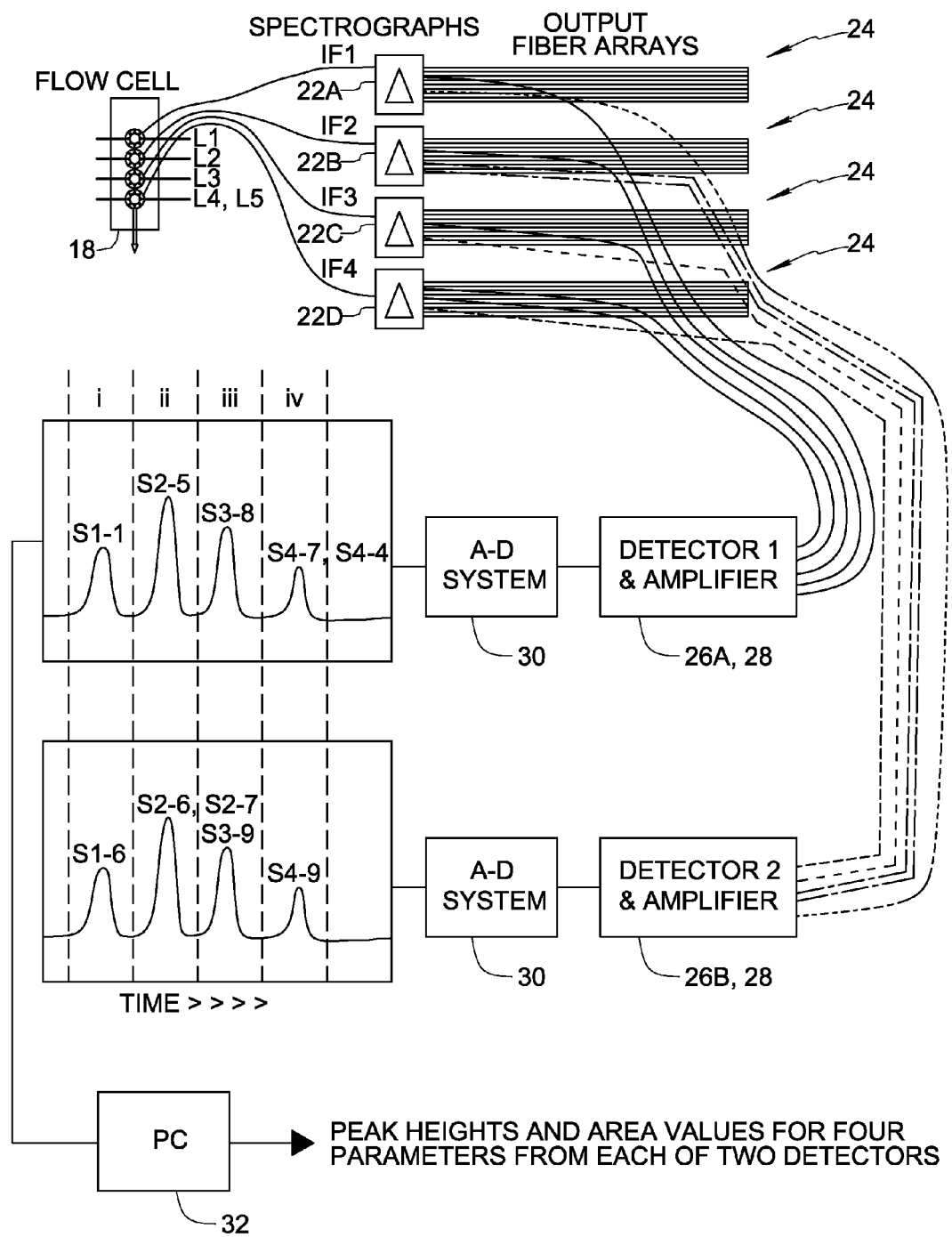
FIG. 2 is a depiction of how signals from different interrogation regions in a flow cell can be combined and detected at single detectors.

FIG. 1 is a block diagram of a flow cytometer 10 formed in accordance with an embodiment of the present invention. Flow cytometer 10 comprises one or more lasers 12 used as excitation sources. The use of more than one laser is common. Beam combining optics 14 are typically used to combine the laser beams, and beam shaping and focusing optics 16 are typically provided to direct the laser beams to a stream of cells flowing through a flow cell 18. Laser light is scattered in all directions. Typically, light scattered in the forward direction (forward scatter) gives information different from that scattered at 90 degrees (side scatter). Both forward scatter and side scatter are commonly measured. Side scattered light and omnidirectional fluorescent light are collected and imaged using light collection and focusing optics 20 (primarily lenses) and efficiently coupled into one or more input fibers IF1-IF4 (FIG. 2). In one embodiment of the invention, light is collected from different sides of the flow cell in an effort to generate a better signal. For example, signal light is normally collected at a first position 90 degrees to the direction of the lasers. An equivalent collection system can be placed at a second position 270 degrees to the direction of the lasers, effectively doubling the light collection efficiency of the system. The input fibers associated with the first and second positions contain the same information and can be combined, effectively improving the sensitivity of the system. The collected multiwavelength light enters a dispersion module 22 which houses wavelength separation optics capable of dispersing incoming light. Typically a diffraction grating or prism is used. Diffraction gratings typically have higher dispersion, have efficiencies that are more wavelength dependent, and have more linear dispersive properties. Prisms have less wavelength dependent efficiencies, but require greater path lengths to disperse the light over a fixed distance and can have a nonlinear wavelength dependent dispersion.

Figure 3:
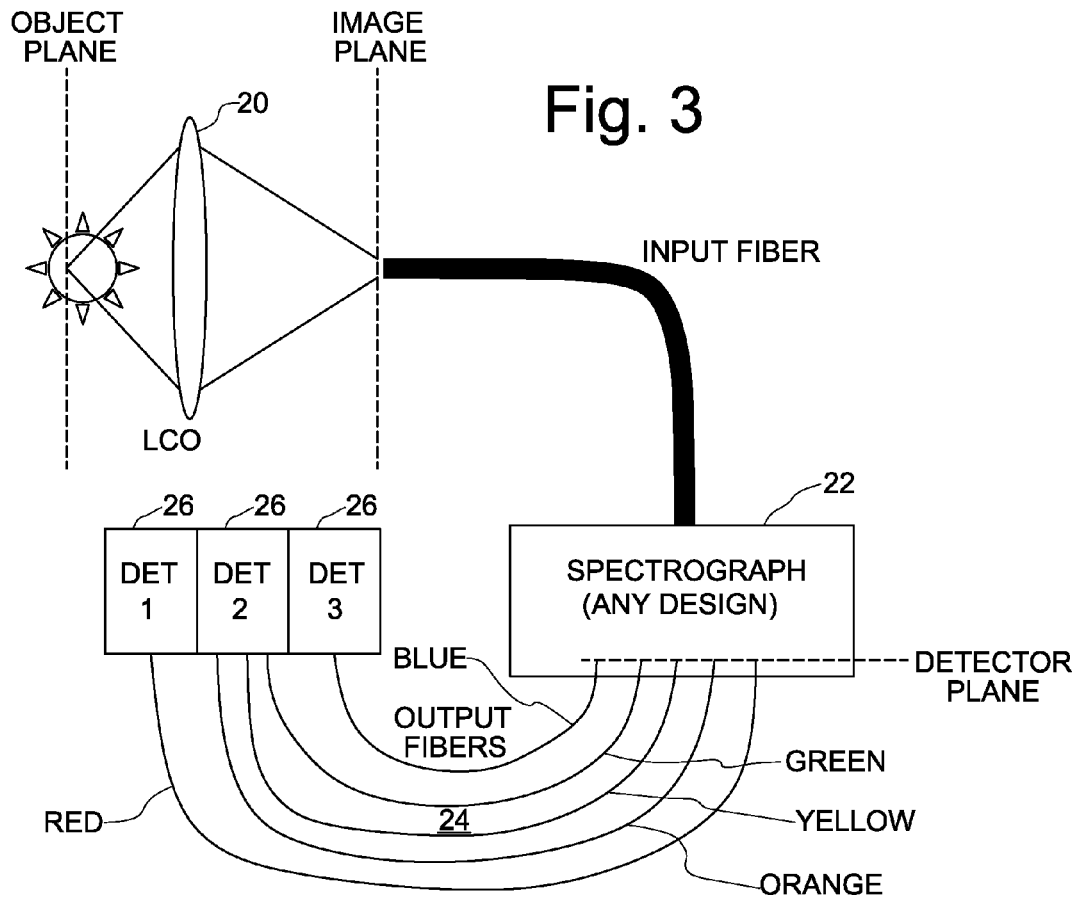
FIG. 3 is a schematic diagram showing a fiber and spectrograph dispersion module arrangement in accordance with an embodiment of the present invention.

FIG. 3 is a schematic depiction of the fiber and spectrograph dispersion module design. An omnidirectional light source located in the object plane has a certain fraction of its signal light (determined by the directional distribution of emitted light and solid angle of the light collecting optics) imaged in the image plane by one or more optical elements (hereafter "light collection optics," or "LCO"). The LCO includes one or more lenses and should be selected and positioned in the most optimum fashion to guarantee: (i) that the most signal light is collected, (ii) that the signal light is delivered to the image plane such that the image spot is smaller than the input fiber's input face, and (iii) that the signal light reaches the image plane guaranteeing that a preponderance of the signal light falls within the numerical aperature ("NA") of the input fiber(s) used.

One or more input fibers are arranged such that the proximal end is placed in the image plane of the LCO and the distal end is placed at the entrance of a spectrograph. The input fibers should ideally be polished at their ends, have antireflection coatings on their ends, have low transmission losses for the desired wavelengths, contain the appropriate cladding layers to limit optical losses, be jacketed to eliminate stray light from entering the fiber, and have a diameter that is as small as possible (without significant loss of signal light). The length of the fiber is not a critical parameter because optical losses in optical fibers are generally small and distances are generally less than a few tens of meters. The NA of the input fibers needs to be matched to the LCO and the spectrograph to assure optimum efficiency.

This invention was conceived to detect objects in a small diameter moving stream which are illuminated by focused laser beams. For the remainder of this specification we will be speaking of a flowing stream example, but the system is equally suitable for a number of other arrangements such as a fixed surface containing an array of fluorescent locations each of which emits light at different wavelengths and/or intensities.

Figure 4A:
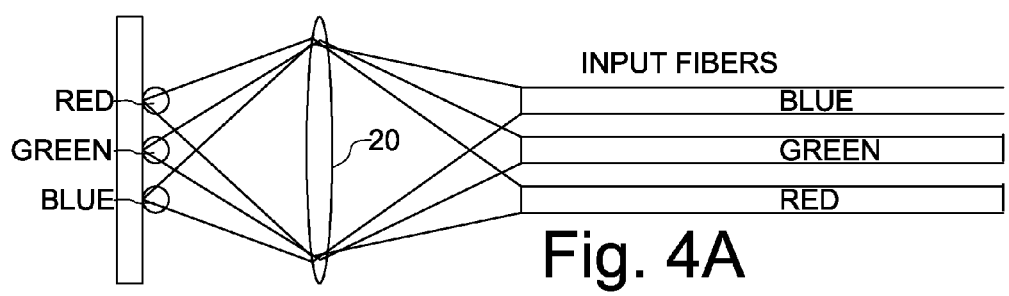
FIGS. 4A and 4B are schematic illustrations showing how light emitted from a set of locations can be collected and imaged to a different set of locations.
Figure 4B:
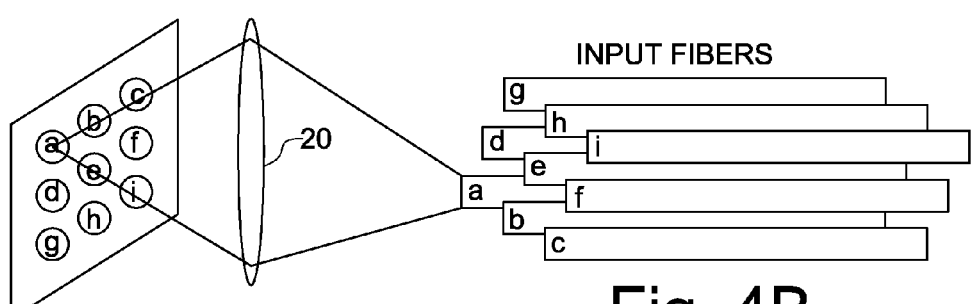

FIGS. 4A and 4B illustrate how light emitted from different locations can be collected and imaged to a different set of locations. FIG. 4A illustrates how light emitted from a plane surface containing three distinct vertically arranged locations can be imaged into a series of fibers. The locations illustrated by the red, green and blue circles in FIG. 4A (top) can be a two-dimensional array of light emitters (FIG. 4B—left) which are, for instance, sensor chemicals, or alternatively (FIG. 4B right), an array of glass tubes or flowing streams which can be illuminated at a specific position along their path. These streams can be held within capillary tubes or constrained by surface topology, surface tension patterning or any other means. The imaging of the source is accomplished with a fixed LCO system including one or more lenses and, in the case of a two-dimensional array of emitters, the input fibers must also be arranged in a two-dimensional array as shown in FIG. 4B.

Figure 5A:
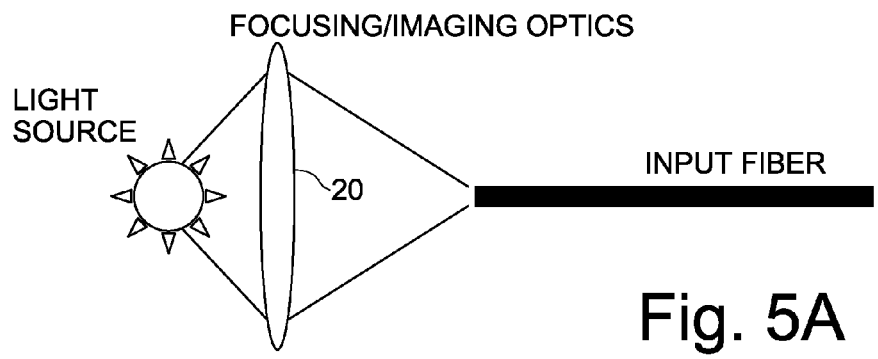
FIGS. 5A, 5B, and 5C illustrate various arrangements whereby light may be detected or routed into fibers.
Figure 5B:
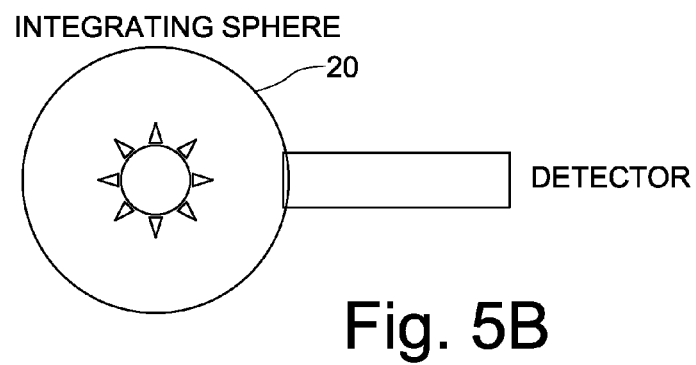
Figure 5C:
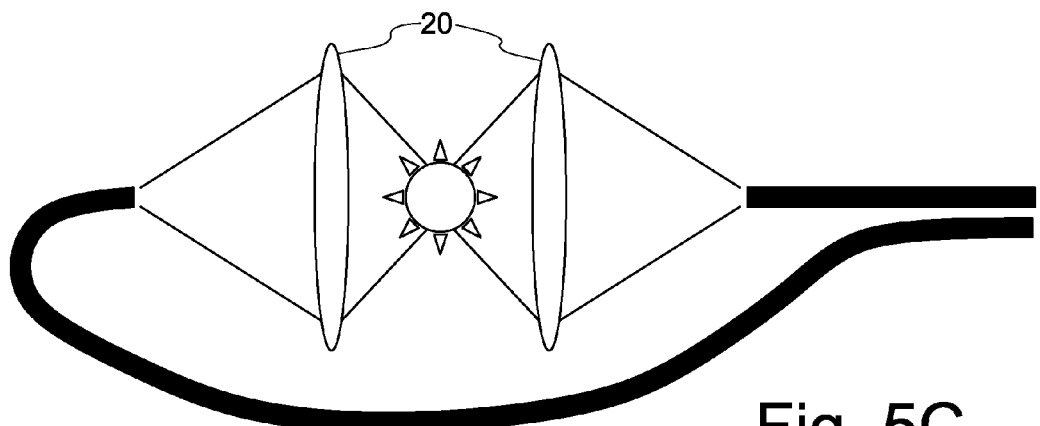

FIGS. 5A-5C conceptually illustrate several different ways that light can be detected or routed into fibers. FIG. 5A illustrates once again the arrangement shown in FIGS. 4A and 4B. FIG. 5B illustrates how an integrating sphere can be used to collect light very efficiently. This arrangement is commonly employed in several optical systems, although this arrangement cannot easily discriminate between light originating from different spatial locations and there is difficulty in directing the collected light to a displaced detector because light strikes the output port at many angles. Much of the light will not couple into a fiber located at the exit port due to the limited numerical aperture (NA) of the fiber. FIG. 5C illustrates how two equivalent focusing/imaging optical systems can be used to significantly increase the amount of light collected and delivered to the detector. Additional focusing/imaging optics and fibers can be used in a variety of different geometries to further increase light collection, as discussed below.

Figure 6A:
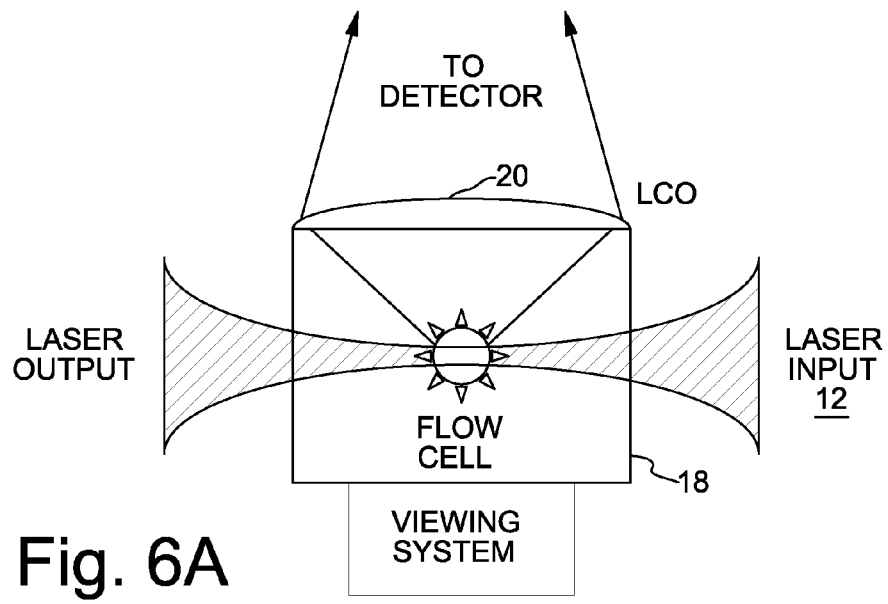
FIGS. 6A and 6B illustrate how the arrangement in FIG. 5C is applied to a flow cytometer.
Figure 6B:
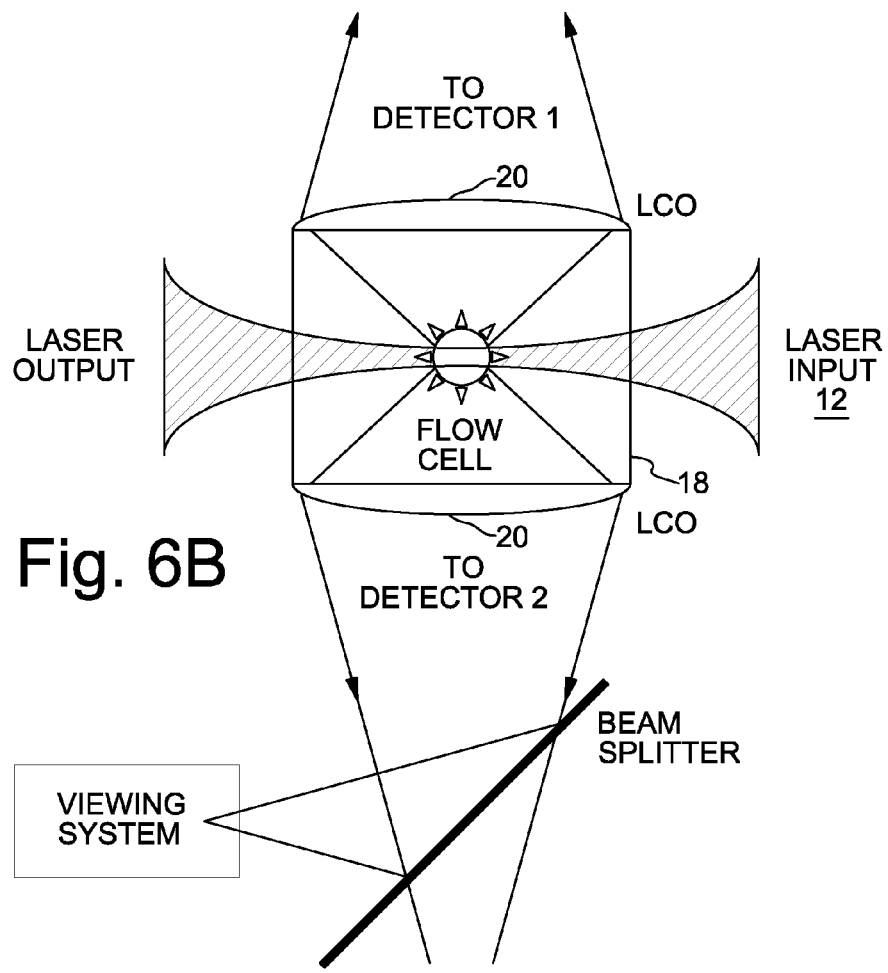

FIGS. 6A and 6B represent how the concept in FIG. 5C is applied to a flow cytometer which is a special application of the present invention. A laser beam is brought into the flow cell which contains a small diameter core stream traveling in a direction into or out of the plane of the paper and also intersects with the focused laser beam. FIGS. 6A and 6B illustrate what happens to a certain fraction of scattered light which is collected and later detected. FIG. 6A illustrates how light is typically collected in a flow cytometer using a single LCO system. FIG. 6B illustrates two parallel systems which, working together, can deliver as much as twice the light to the detectors. Placing an optional beam splitter in one path allows the user to directly image the flow cell for diagnostic purposes with a loss of light depending upon the amount of light reflected by the beam splitter.

Figure 7:
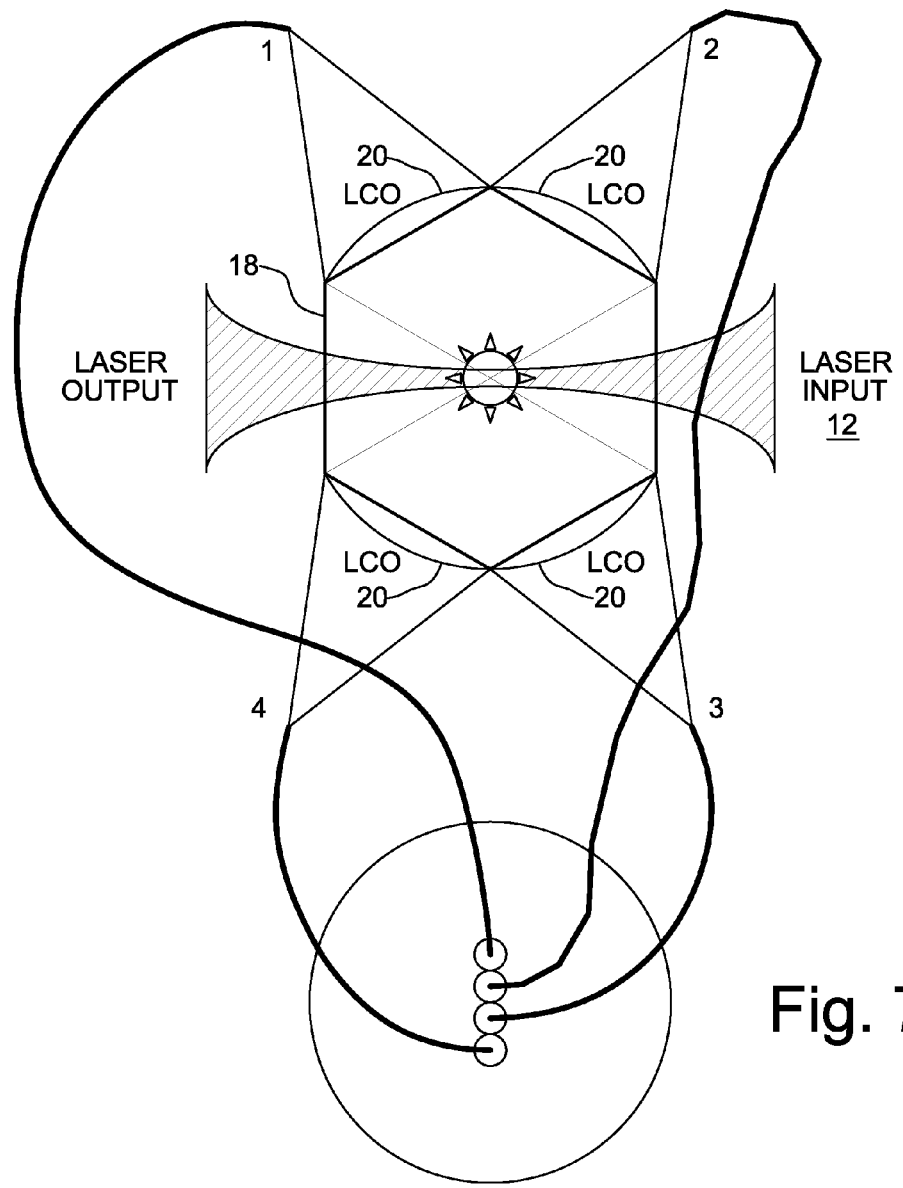
FIG. 7 shows a flow cell that is hexagonal in cross-sectional shape.

FIG. 7 shows a flow cell that is hexagonal in cross-sectional shape and affords the opportunity to collect even more light. The four LCO/fiber systems in this arrangement are equivalent and still provide for laser input and output windows (right and left) and stream input and output surfaces (top and bottom of flow cell, parallel to drawing page). The output fibers are shown in bundles which could contain one or more individual input fibers.

Figure 8A:
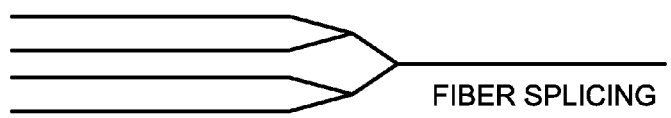
FIGS. 8A and 8B illustrate two configurations by which light from four fibers may be combined to one distal output.
Figure 8B:
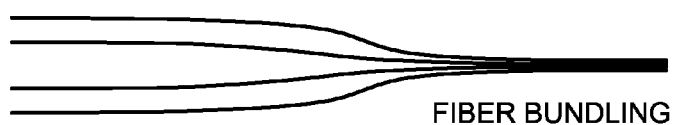

FIGS. 8A and 8B illustrate two configurations by which to combine light from four fibers to effectively one distal output. In the configuration shown in FIG. 8A the fibers are actually spliced together, whereas in the configuration shown in FIG. 8B the fibers are simply bundled together. The splicing method is conceptually simpler, but there are optical losses with the splicing making it less efficient overall.

While the design in FIG. 7 has six-fold radial symmetry, other designs are clearly possible, for instance the laser input and output faces could be smaller than the other 4 faces permitting greater light collection efficiency.

Figure 9A:
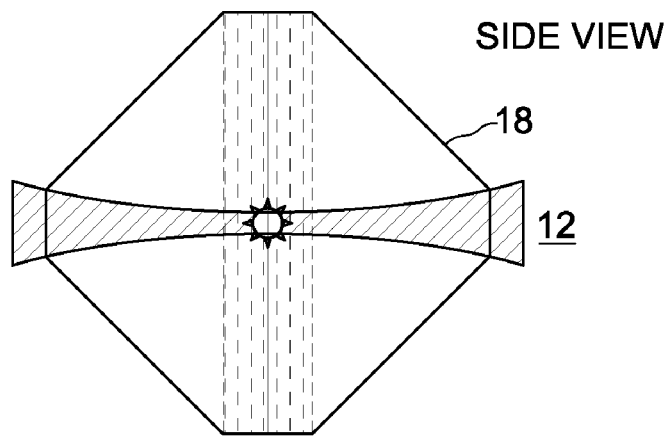
FIGS. 9A and 9B are side and top views, respectively, of an alternative flow cell design providing greater light collection efficiency.
Figure 9B:
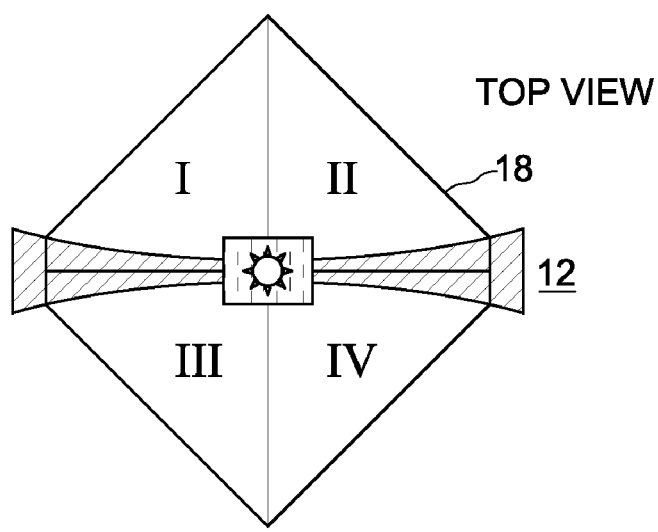

Another flow cell design is shown in FIGS. 9A and 9B which, although more difficult to construct, provides for even greater light collection efficiency. The depicted flow cell has eight light collecting faces: I, II, III, IV as shown with another four faces directly below faces I, II, III, IV. Round lenses can be shaped to fit onto the faces and coupled with index matching liquids or gels to maximize light collection efficiency. Alternatively, a flow cell of this complexity could be molded from a polymer with potentially some secondary machining/polishing procedures to fabricate the final design. While flow cells containing more than eight faces can be envisioned, the cost/benefit of this added complexity must be determined.

Coupling light from different faces is easily accomplished with fiber optics.

It is recognized that it is possible to use Bragg gratings in the fiber to further adjust which wavelengths pass through the system. This technology could be effectively used to omit (for instance) the laser light illuminating the flow stream or another wavelength that is otherwise undesirable.

The distal end of the input fiber is inserted into a spectrograph dispersion module of any design so long as it is designed to accept the input fiber with a minimum of optical losses. The spectrograph may be equipped with an additional (more restrictive) input slit commonly used to improve resolution, although use of such a slit will result in optical losses. If the diameter of a single input fiber (or alternatively, the diameter of fibers arranged vertically and tightly packed as in FIG. 7) is sufficiently small, no slit is required and efficiency will be at an optimum. In this case the fiber diameter(s) is the effective slit width. Slit width dependence upon spectrograph resolution is well described in the literature. A spectrograph often has an input aperture to increase spectral resolution at the expense of overall efficiency. This aperture can be enlarged to improve efficiency with a concomitant loss in resolution depending upon the application. In cases where efficiency is very important and resolution not all that important, the input fiber(s) can serve as its own aperture. All other parameters being equal, a smaller diameter fiber will provide better resolution.

The optics of the spectrograph must be designed around the numerical aperture of the input fiber and the position where it will be secured when in operation or vice versa. The spectrograph may be of any design or size although there will be variations in throughput efficiency, resolution, wavelength range, center wavelength, cost, compactness, etc.

Regardless of the design, all spectrographs disperse the incoming light according to wavelength. All spectrographs are limited in what wavelength range is delivered to the detector plane. A spectrograph's optics are chosen carefully to provide the most optimum performance. Among the many specifications that a spectrograph is characterized by, are the wavelength range, dispersion, optical resolution, and the number of elements in the detector. Generally, incoming light is dispersed and focused onto the detector plane (shown in FIG. 3). The detector plane is drawn as a straight horizontal line, but wavelength dispersion arising from the optics found in the spectrograph may cause the focal positions of different wavelengths of light to be focused at slightly different distances causing the actual focal plane to be more complicated than a simple horizontal straight line. The use of aspheric and achromatic optics can be used to minimize or eliminate this problem. The output fibers can be positioned to largely accommodate these differences in wavelength dependent focal position. In the current invention, output fibers are placed at the detector plane in an effort to (i) capture as much of the light as possible and (ii) obtain as high a resolution as possible.

Longer wavelengths focus to a slightly larger spot and it is anticipated that the longer wavelengths might be better collected by slightly larger output fibers. Employing fibers of different sizes (even mixing them) could be used for a variety of reasons (described below).

Figure 10B:
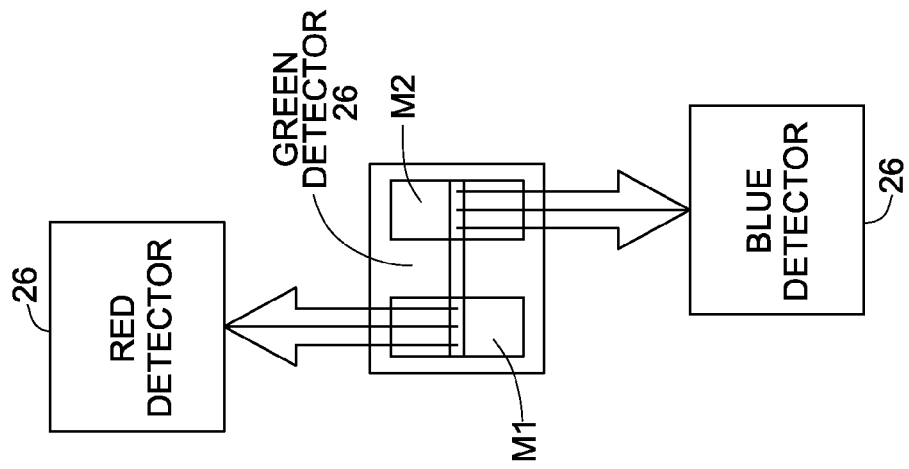
FIGS. 10A and 10B show an arrangement by which three different hypothetical wavelength regions may be routed to different detectors using mirrors.
Figure 10A:
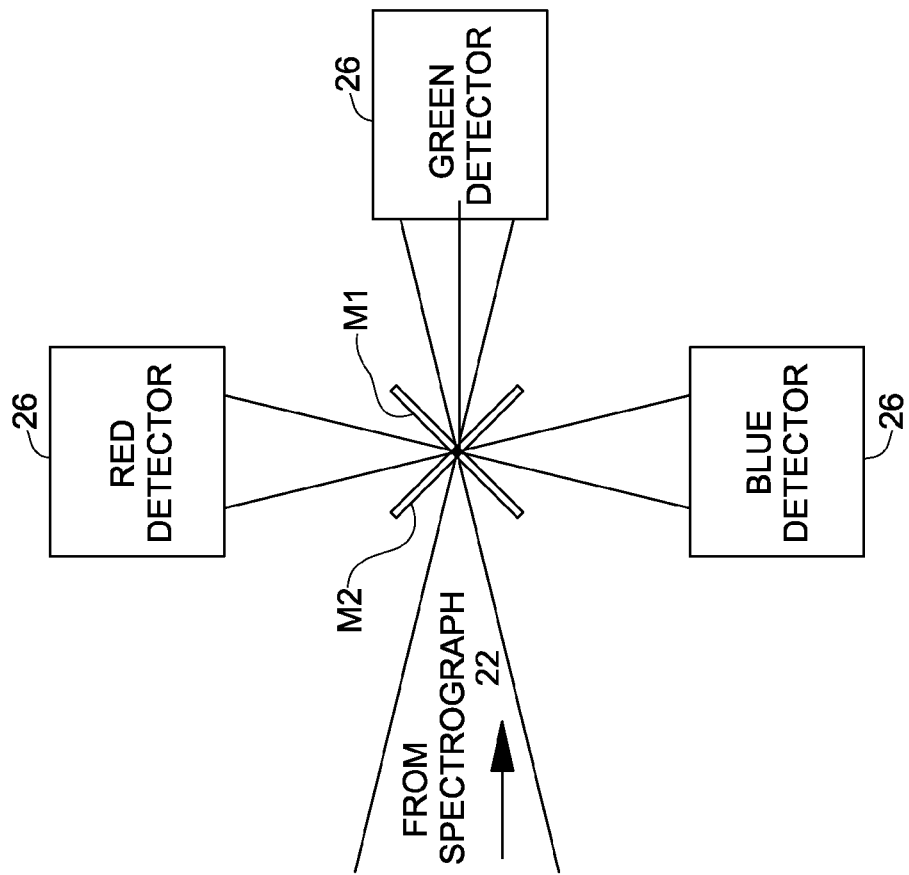

One simple and primitive design (not using fibers) is to use a set of fully or partially reflective mirrors (located at the detector plane to steer signal light of different wavelengths to detectors placed at positions other than at the detector plane as shown in FIGS. 10A and 10B which illustrates three hypothetical wavelength regions shown in blue, green and red. FIG. 10A is the side view of two mirrors placed at 45 degrees to the incoming dispersed signal light. The red mirror M1 directs the red light upward to a single element detector while the blue mirror M2 directs the blue light downward to a different detector. Green light does not see a mirror and is allowed to pass to the green detector. FIG. 10B is the same device as seen from the spectrograph with the mirrors shown as fully reflective mirrors. The number of spectral regions can be easily expanded by arranging additional mirrors. A more sophisticated and flexible option is to use a one- or two-dimensional mirror array which could be computer controlled to deliver different wavelength bands to different output fibers. Commercially available mirror arrays have close to or more than 1,000,000 individually controlled mirrors and present a option for excellent resolution and extremely good application flexability.

Reference is also made to FIG. 2. In either case, once the incoming light is dispersed, it is focused onto an array of output fibers 24 wherein each output fiber contains a particular range of wavelengths. The output fibers 24 can be placed in contact with one another in a linear array or each positioned uniquely. The output fibers 24 are typically multimode fibers to facilitate efficient coupling and overall alignment stability (multimode fibers are less sensitive to temperature changes and other sources of misalignment). Arranging the output fibers 24 in a close packed array minimizes losses at fiber to fiber junctions and permits all wavelengths over a fixed range to be efficiently collected into the output fibers. The output fibers 24 are coupled at their exit ends to one or more light sensitive detectors 26 each having an associated amplifier circuit 28 and analog-to-digital signal conversion circuit 30, whereby light signals are detected and converted to digital form. The digital signals are then input to a computer 32 for analysis thereof.

The diameter and number of output fibers 24 can vary to some degree. For a given range of emission wavelengths to be detected, for instance 400 nm, a grating is chosen that disperses this range of wavelengths efficiently and distributes them over a distance of (for instance) 1 cm at a distance 10 cm from the grating. A lens (not shown) is placed after the grating to focus the signal light at the input faces of the output fibers 24. The result of the dispersion module 22 and focusing optics is a streak of light with the light distributed accorded to wavelength. Placing a close packed array of 1 mm diameter output fibers at this distance permits (in this example) approximately 40 nm bandwidth of light to be placed into each of 10 fibers. There is some small overlap depending upon the resolution attainable by the dispersion module 22 which is largely dependent upon the input fiber's diameter (effectively the slit width of the dispersion module). In principle, a greater number of smaller diameter output fibers 24 could be used to reduce the wavelength range in each output fiber. However, this strategy will ultimately increase the coupling losses at the junctions between adjacent fibers and ultimately above and below the output fibers when the output fiber diameters become smaller that the focused light streak. Alternatively, a two dimensional bundle of smaller fibers can be used. Alternatively, for users who measure the same signals all the time, fibers of different sizes could be employed each placed in a fixed position along the streak in an effort to collect known signals.

Alternatively, output fibers of the same or different sizes could be freely positioned along the streak to optimize the collection of signals at known wavelengths.

Alternatively, a one or two dimensional system of adjustable micromirrors could be used in place of the output fibers, reflecting the signal light to one or more detectors 26 suitably arranged. This version of the device could either employ fixed position mirrors or computer controlled mirrors permitting the user greater flexibility. The mirrors could be free to move in one or two axes.

Although it is common to have round fibers based upon the methods of fabrication and the need to minimize transmission losses, fibers of different cross-sectional shapes may be used to increase coupling efficiency by minimizing losses at fiber-to-fiber junctions.

Figure 11A:
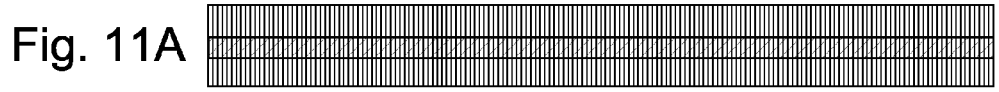
FIGS. 11A-11I illustrate various array configurations and geometries of detectors and/or fibers for receiving dispersed light at the detector plane in a spectrograph dispersion module.
Figure 11B:
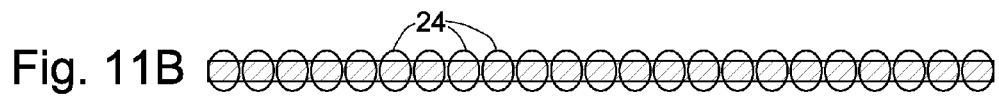
Figure 11C:
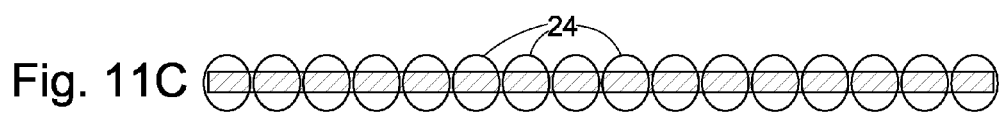
Figure 11D:
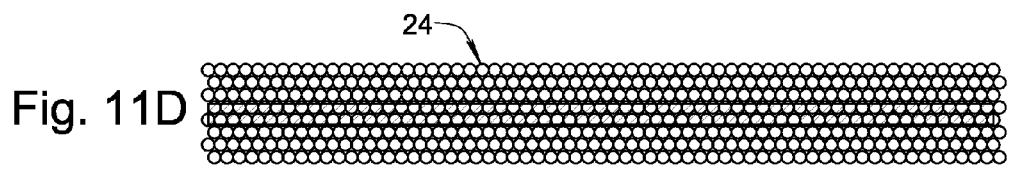
Figure 11E:
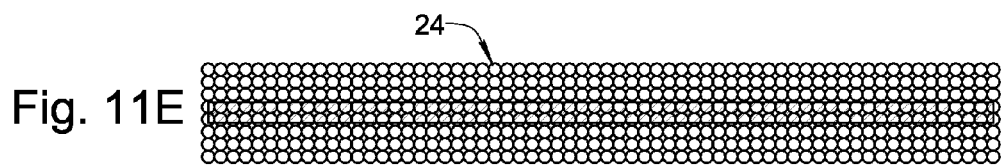
Figure 11F:
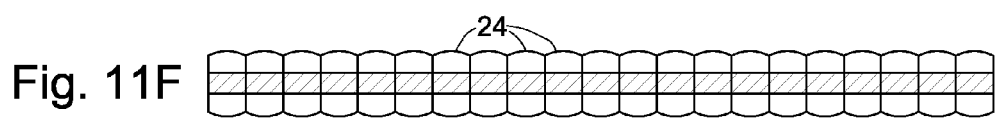
Figure 11G:
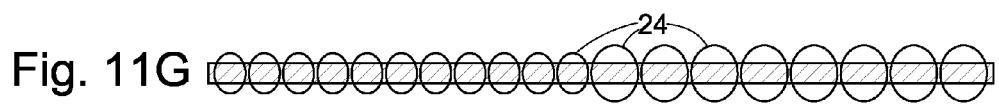

The use of optical fibers to collect and distribute the spectrally resolved signal light has several advantages which are discussed below. Dispersed light reaching the detector plane in a spectrograph can be detected using a linear array of generally rectangular detectors as illustrated in FIG. 11A. FIG. 11B illustrates a linear array of output fibers with no or negligible space between fibers. The output fibers in all cases should have a fiber cladding layer important to minimize crosstalk between fibers, but should also be limited in thickness to guarantee the highest efficiency. FIG. 11C represents how increasing the diameter of the fibers minimizes losses at fiber junctions, but also increases the wavelength range of each fiber. FIG. 11D represents a close packed arrangement of small diameter fibers and FIG. 11E represents a row and column arrangement of the same fibers which will not be as efficient, but offers slightly better resolution. FIG. 11F represents the use of fibers whose input tip geometry has been modified to minimize the interfiber spaces where light losses occur. The precise shaping of the fiber into a noncircular cross-section must also take into account the amount of light lost in fiber transmission arising from noncircular crossections. A particular fiber geometry which could be used and has been discussed is a hexagonal crossections. This shape has particular good packing efficiencies. FIG. 11G represents the use of fibers of different sizes.

Figure 11H:
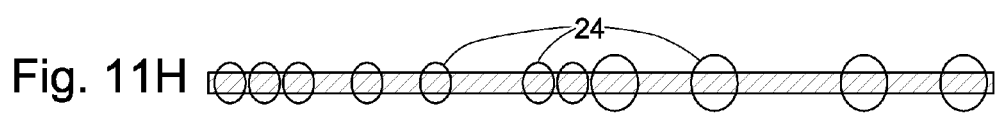

FIG. 11H represents the use of different sized fibers where there are gaps between fibers shown. This design is useful where it is known in advance what signals are to be detected; fibers (potentially of different diameters) could be positioned and secured in their ideal positions matching the center wavelengths of the fiber and the spectral emission. The range of the emission can be matched by choosing the fiber diameter. For instance, a fluorescent dye known to have its emission curve centered about a particular wavelength and having a known bandwidth can be matched to one or more fibers having the necessary width and positioned appropriately. These fibers could be preset and held rigidly or independently positioned mechanically or through motors as the user requires. Optical tuning of the entire spectral bandwidth can be accomplished through the movement of optics in the spectrograph (for instance the grating) or by translation of the entire output fiber assembly.

Figure 11I:
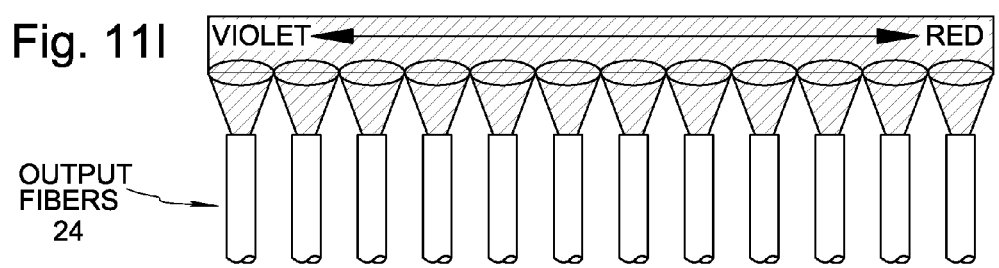

FIG. 11I represents the special case where optical elements, such as lenses, may be used to subsequently focus light in one or two axes in an effort to minimize light from falling between two adjacent fibers. The lenses can be of several types, and the goal may be accomplished for example with lenticular lenses. Shown in FIG. 11I is light striking optical elements which focus light onto the input faces of an array of optical fibers.

As in the case of the input fibers, for signal light to efficiently enter the output Fibers, it is necessary that the light striking the fibers faces not be outside the numerical aperture (NA) of the fibers. Placing an antireflection coating on these fiber faces will also increase efficiency. A relatively thin cladding layer will also improve overall performance. The front end of the output fibers should be placed in a housing to prevent stray light from entering the fibers in the absence of a jacket. Outside this housing, where the fibers need not be closely packed, sufficient room will exist for the individual fibers to be jacketed to prevent stray light from entering the fibers.

Once inside the output fibers, the light can be transported over fairly large distances (tens of meters) without significant loss and directed in virtually any direction provided the minimum bend radius of the fibers is not exceeded. Collecting the light into output fibers permits the detectors to be located in a more convenient location and, in the case that they are large with respect to the dimensions found at the detector plane, making it possible to use detectors which do not fit within the detector plane.

A given fluorescence light signal may be found in more than one fiber either because the spectral width of the light signal is larger than the input wavelength range of a single fiber or because no single fiber is positioned to precisely match the wavelength range of the fluorescence light. Therefore, to efficiently detect the weakest signals, it may be desirable to combine the light output from two or more adjacent fibers and direct their light to a common detector.

Similarly, light signals from other interrogation regions and hence, from other output fiber sets, can be similarly combined at a common detector 26. If the detector's area is sufficiently large, it may be possible to physically bundle all the desired output fibers and place their terminal ends in such a manner to efficiently detect all the signals. If there are too many fibers to conveniently or efficiently detect all the signals adequately, it may be necessary to use lenses attached to the output fiber ends (or placed in close proximity to the output fiber ends) to collimate (or focus at some distance) the exiting light from each of the output fibers. It may be necessary to arrange the output fibers at different incidence angles and/or distances to the detector to accommodate all the fibers required. It may be desirable to use one or more wavelength selective filters between the output fibers and the detector to remove unwanted wavelengths to potentially improve signal-to-noise in the measurements.

Figure 12A:
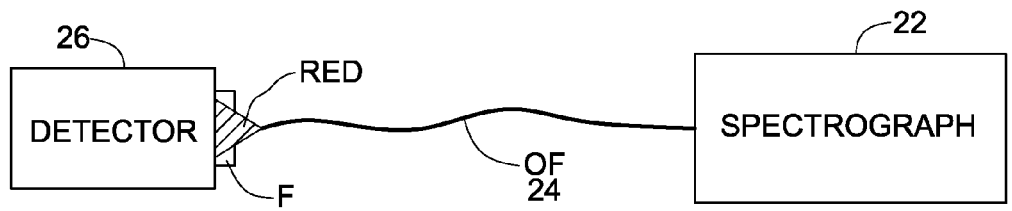
FIGS. 12A-12C show alternative configurations whereby fibers may be used to feed light signals to a detector of fixed active area.
Figure 12B:
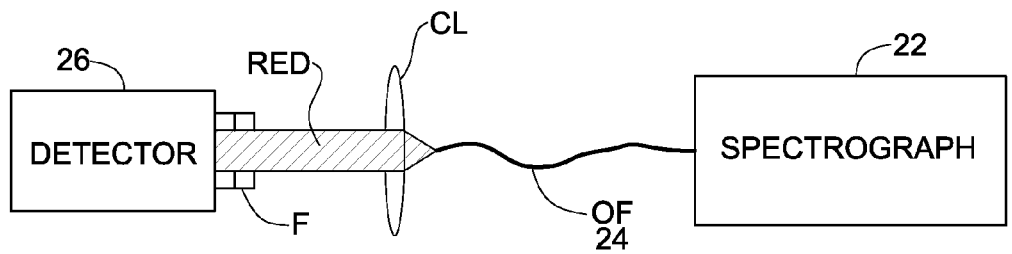
Figure 12C:
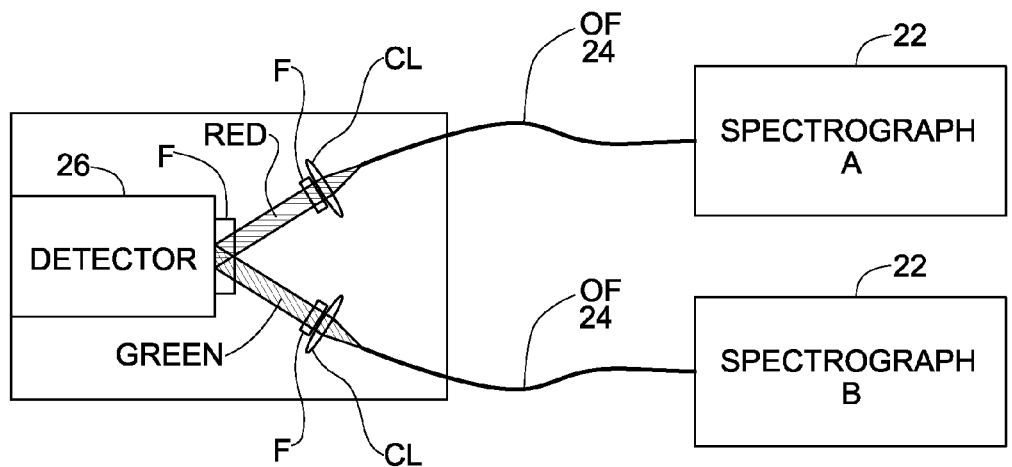

FIGS. 12A-12C illustrates how fibers can be used to feed light signals to a detector of fixed active area. FIG. 12A illustrates the most trivial case where signal light from one fiber reaches a detector. In our experience it is desirable to have optional optical filters after the fibers to eliminate light that is completely outside the spectral range expected in the fiber which can result from scatter in the spectrograph, or to further restrict the wavelengths directed into a fiber of fixed dimensions. In this case, an absorptive filter is suitable because it is not angle-of-incidence dependent. If incident angle dependent filters are chosen for use, FIG. 12B demonstrates the use of a simple lens which can be positioned such that the light is significantly less divergent (particularly important if a small area detector is used). The lens is also useful for occasions when the filters are thick or more than one filter needs to be used. In these cases, light exiting the polished end of a fiber may overfill the detector.

It may be necessary or desirable to combine two or more adjacent fibers to expand the range of wavelengths or combine fibers from different spectrographs as in FIG. 12C. FIG. 12C illustrates two fibers from different spectrographs combined at a single detector. The two fibers could have just as easily come from the same spectrograph. The fibers are fed into the detector collection block at specific angles and held rigidly at angles such that both their light is incident at a detector's active area. The use of a collimating lens permits the output fiber's distal ends to be some distance from the detector. The angle between the fibers should be as small as is practically possible so that reflections from the detector window are kept at a minimum and the projection of light onto the detector is as close to a circle as possible. The lens and the fiber-specific optional filters have definite size and can be obstacles to adjacent components if too close to one another. The use of a lens permits the fibers' distal ends to be some distance from the detector and prevent them from being in each other's way.

Figure 13:
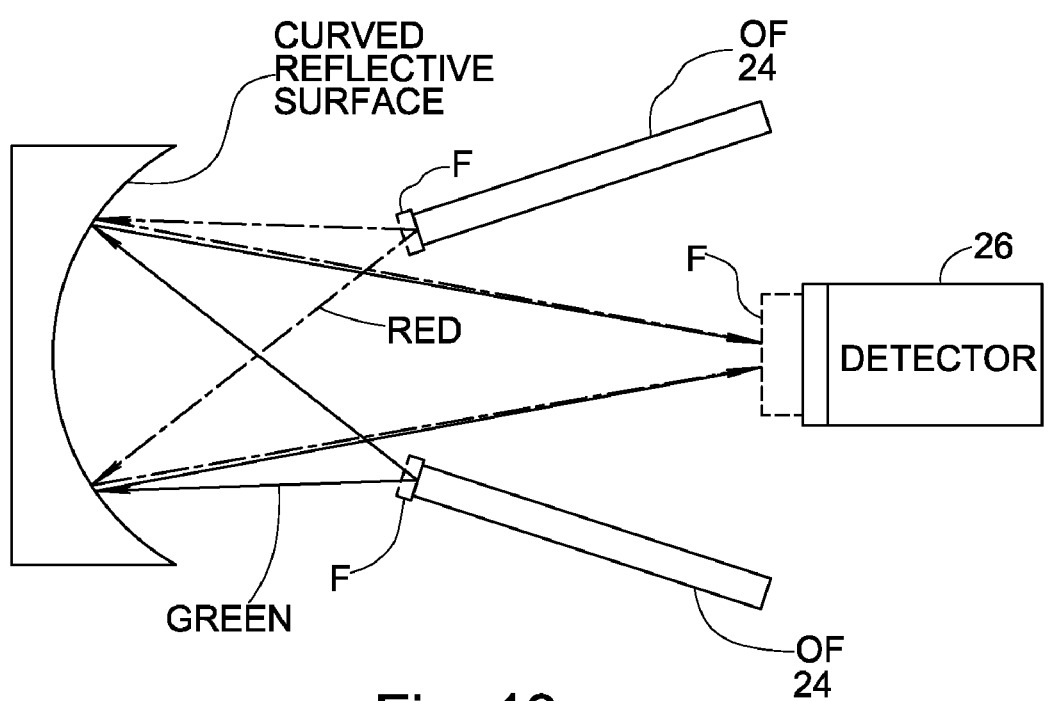
FIG. 13 illustrates a configuration utilizing a concave mirror whereby numerous output fibers can be combined at a single detector.

The addition of these optical elements will result in additional optical losses. Their value in improving the quality of the signal should be considered in light of any optical losses they impose. As discussed previously, a Bragg grating in the fiber could be used to increase the signal-to-noise and reduce or eliminate the need for extra filters. It is clear that optics should be antireflection coated when possible and a minimum of surfaces should be employed to minimize signal attenuation. In this manner, numerous output fibers can be combined at a single detector. One unique geometry utilizing a concave mirror is shown in FIG. 13. This design has the advantage of being potentially more efficient.

As discussed, it is possible to combine signals arising from different interrogation regions since they are generated at different times and hence distinguished from one another. The strength of scatter and fluorescence signals can vary over several orders of magnitude. While some effort should be made to combine signals of similar strength to the same detector, a logarithmic amplifier is capable of expanding the dynamic range of the detectors. It is also possible to optically attenuate bright signals through a variety of means including the use of filters, cross polarizers, smaller output fibers, etc.

It is important to appropriately position the focused laser beams defining the interrogation regions so that a cell or other object passes through the interrogation regions at known times. The time between interrogation regions is dependent upon the flow velocity and the distance between the interrogation regions. The input fibers are preferably arranged a fixed distance from each other and helps to define the spacing of the interrogation regions. In this example, the time elapsed when a cell travels from one interrogation region to the next is inversely proportional to the flow velocity. Preferable flow velocities are those that produce stable (laminar) flow conditions and permit sufficient numbers of cells to be measured per unit time. The elapsed time between interrogation regions must also permit the detector and amplifier circuits to sufficiently recover from the signal generated at the preceding interrogation region. The simplest embodiment is to hold the sheath liquid constant to establish a stable flow velocity and to alter the core pressure to adjust the core stream width and adjust the number of events recorded per unit time.

A logarithmic amplifier can require a longer time to recover particularly from a bright signal. We have found that slowing the flow velocity to create a 12 microsecond delay between signals from adjacent interrogation regions is adequate, but it could be as short as 3 and as long as 100 microseconds as long as this value is fixed and permits the amplifiers sufficient time to recover.

Preferably, the scattered light signal from the first interrogation region is used as a trigger for the data acquisition system to initiate data collection. Preferably, an analog to digital converter operating at greater than 1 Megasamples per second begins to collect data. Data is collected for a time period equal to the number of interrogation regions multiplied by the time interval between interrogation regions.

The sample concentration can be adjusted so as to minimize the likelihood that two cells will be optically illuminated at the same time by any of the lasers. Being a statistical process, this may still occur at some frequency even at low sample concentrations. It is possible to detect most of these events and disregard the data by measuring the signal strength at the end of all time intervals and assuring oneself that the signal has dropped to a preset level consistent with anticipated detector/amplifier signal recovery.

The collected data for a single event will then comprise intensity versus time records (one record for each detector). The intensity versus time data is further divided into n intervals and the associated peaks analyzed for their heights and areas. In this manner, as many as n different signals are measured by each detector.

There are important advantages of having multiple interrogation points and an equal number of dispersion modules 22 and output fiber arrays. FIG. 2 illustrates an embodiment where there are four interrogation points illuminated by five lasers (laser 4 (L4) and laser 5 (L5) illuminate the same point). The interrogation points are imaged onto four input fibers IF1-IF4 each delivering multispectral light to a different dispersion module 22A-22D, wherein the dispersion modules are each in the form of a spectrograph. The dispersion gratings in each spectrograph can be chosen to match the range of expected wavelengths delivered by the input fiber(s).

In this example, there are only two detectors 26A, 26B each of which has several output fibers 24 leading to it. A given particle flowing through the flow cell will encounter each of the four interrogation zones in regular succession. The time interval between the interrogation points will depend directly upon the velocity of the stream and the distance between the interrogation points.

Each of the detectors 26A, 26B has at least one output fiber from each spectrograph 22A-22D. Detector 26A has output fibers S1-1, S2-5, S3-8, S4-7 and S4-4 and detector 26B has output fibers S1-6, S2-6, S2-7, S3-9, and S4-9 where, for example, S1-6 is the signal from the $6^{th}$ output fiber in spectrograph 22A.

Signal S1-1 can be used to collect side scattered or forward scattered light. This relatively strong signal is easily detected and occurs first and can therefore be used to trigger data collection on all other detectors. The fact that the $6^{th}$ and $7^{th}$ fibers of spectrograph 22B are used in detector 26A reflects that the emission bandwidth of that signal is wider than is distributed over a single output fiber. The fact that the $7^{th}$ and $4^{th}$ fibers (noncontiguous fibers) from spectrograph 22D deliver light to detector 26A is useful when: (1) one laser (L4 or L5) is generating two spectrally separated signals or (2) L4 and L5 produce two spectrally resolved signals. Since, in either of these two cases, the signals arrive at the same time, it is easier to interpret the data if the two possible signals are not present in the same event which is possible for certain sample types.

For those events that occur at the same time (from the same event), it is better that they be divided among the different detectors so that they can be measured individually.

It is recognized that the number of events per unit time may need to be adjusted (primarily through concentration and sample stream diameter) so that the chance of two events overlapping in time is low. If and when this does occur, these data points can be rejected as unreliable.

A fast A-D system 30 can be used to sample the output signal of the detector/amplifiers and be logically divided into different time domains (in this case 4 domains: i, ii, iii, iv). The peak height and area of each signal peak (and any other relevant parameters) can be calculated. These values can be stored in a much smaller computer file.

What is claimed is:

1. A flow cytometer comprising:
a flow cell through which a fluid sample flows, the fluid sample containing particles to be detected, the flow cell including a plurality of different interrogation regions spaced from one another along a direction of sample flow, each of the plurality of interrogation regions being illuminated by a respective excitation beam, wherein the flow cell is configured such that the particles to be detected are carried in a stream successively through each of the plurality of interrogation regions;
at least one excitation light source, each excitation light source emitting an excitation beam for illuminating at least one of the interrogation regions in the flow cell;
at least one input fiber for each interrogation region, each input fiber receiving scattered light and fluorescent light from its associated interrogation region, wherein each input fiber is arranged to receive light scattered or emitted in directions out of an interrogation plane defined by an axis of the respective excitation beam and the direction of sample flow;
a dispersion module for each interrogation region, each dispersion module being coupled to the at least one input fiber for the interrogation region with which the dispersion module is associated, the dispersion module including an optical element that disperses incoming light from the at least one input fiber coupled to the dispersion module;
a plurality of output fibers for each dispersion module, each of the plurality of output fibers receiving light in a unique spectral range from the dispersion module with which the output fiber is associated; and
at least one photosensitive detector for receiving light transmitted by the output fibers and generating signal information in response to the received light.

2. The flow cytometer according to claim 1, wherein the flow cytometer comprises a plurality of excitation light sources, wherein each of the plurality of interrogation regions is illuminated by a respective excitation beam having a unique wavelength.

3. The flow cytometer according to claim 2, wherein at least one of the plurality of interrogation regions is illuminated by more than one excitation light source.

4. The flow cytometer according to claim 1, wherein the flow cytometer comprises a plurality of input fibers for at least one of the plurality of interrogation regions.

5. The flow cytometer according to claim 1, wherein the flow cytometer comprises a dispersion module wherein the optical element is a diffraction grating.

6. The flow cytometer according to claim 1, wherein the flow cytometer comprises a dispersion module wherein the optical element is a prism.

7. The flow cytometer according to claim 1, wherein the flow cytometer comprises only one photosensitive detector.

8. The flow cytometer according to claim 1, wherein the flow cytometer comprises a plurality of photosensitive detectors.

9. The flow cytometer according to claim 1, wherein light from a group of the output fibers is combined and directed onto a single photosensitive detector.

10. The flow cytometer according to claim 9, further comprising lenses associated with the group of output fibers for directing divergent light exiting the group of output fibers onto the single photosensitive detector.

11. The flow cytometer according to claim 9, further comprising at least one mirror associated with the group of output fibers for directing divergent light exiting the group of output fibers onto the single photosensitive detector.

12. The flow cytometer according to claim 11, wherein the at least one mirror includes an array of adjustable mirrors.

13. The flow cytometer according to claim 1, further comprising one or more optical filters for attenuating light from at least one of the plurality of output fibers.

14. The flow cytometer according to claim 1, wherein the directions out of the interrogation plane include a direction normal to the interrogation plane.

15. The flow cytometer according to claim 1, further comprising at least one lens associated with each input fiber for collecting light from the associated interrogation region.

16. A flow cytometer comprising:
- a flow cell through which a sample flows, the flow cell including a plurality of different interrogation regions spaced from one another along a direction of sample flow, each of the plurality of interrogation regions being illuminated by a respective excitation beam;
- at least one excitation light source, each excitation light source emitting an excitation beam for illuminating at least one of the interrogation regions in the flow cell;
- at least one input fiber for each interrogation region, each input fiber receiving scattered light and fluorescent light from its associated interrogation region, wherein each input fiber is arranged to receive light scattered or emitted in directions out of an interrogation plane defined by an axis of the respective excitation beam and the direction of sample flow;
- a dispersion module for each interrogation region, each dispersion module being coupled to the at least one input fiber for the interrogation region with which the dispersion module is associated, the dispersion module including an optical element that disperses incoming light from the at least one input fiber coupled to the dispersion module;
- a plurality of output fibers for each dispersion module, each of the plurality of output fibers receiving light in a unique spectral range from the dispersion module with which the output fiber is associated;
- at least one photosensitive detector for receiving light transmitted by the output fibers and generating signal information in response to the received light; and
- at least one amplifier connected to the at least one photosensitive detector, wherein the at least one amplifier is used to resolve the signal information generated in response to light from at least two output fibers associated with different dispersion modules with respect to time.

17. The flow cytometer according to claim 16, wherein the at least one amplifier includes a non-linear amplifier.

18. The flow cytometer according to claim 16, further comprising at least one analog-to-digital conversion circuit connected to the at least one amplifier and a computer connected to the at least one analog-to-digital conversion circuit.

* * * * *